United States Patent
Makino et al.

(10) Patent No.: US 9,067,048 B2
(45) Date of Patent: Jun. 30, 2015

(54) MEDICATION LIQUID SUPPORTING JIG AND METHOD OF APPLYING MEDICATION TO MICRO-NEEDLE USING SAME

(75) Inventors: Yuji Makino, Kagawa (JP); Takurou Kurita, Kagawa (JP); Hidetoshi Hamamoto, Kagawa (JP)

(73) Assignee: MEDRx Co., Ltd., Higashikagawa (JP)

( * ) Notice: Subject to any disclaimer, the term of this patent is extended or adjusted under 35 U.S.C. 154(b) by 784 days.

(21) Appl. No.: 13/265,997

(22) PCT Filed: Apr. 24, 2010

(86) PCT No.: PCT/JP2010/002967
§ 371 (c)(1), (2), (4) Date: Dec. 16, 2011

(87) PCT Pub. No.: WO2010/122816
PCT Pub. Date: Oct. 28, 2010

(65) Prior Publication Data
US 2012/0080119 A1 Apr. 5, 2012

(30) Foreign Application Priority Data
Apr. 24, 2009 (JP) ................................. 2009-106535

(51) Int. Cl.
*B01L 3/00* (2006.01)
*G01N 31/16* (2006.01)
(Continued)

(52) U.S. Cl.
CPC .......... *A61M 37/0015* (2013.01); *A61K 9/0021* (2013.01); *A61M 2037/0053* (2013.01)

(58) Field of Classification Search
USPC ........................................... 422/553; 269/38
See application file for complete search history.

(56) References Cited

U.S. PATENT DOCUMENTS

| 5,716,842 A | 2/1998 | Baier et al. |
| 2002/0132054 A1* | 9/2002 | Trautman et al. .......... 427/372.2 |

(Continued)

FOREIGN PATENT DOCUMENTS

| DE | 44 35 107 C1 | 4/1996 |
| EP | 2 153 863 A1 | 2/2010 |

(Continued)

OTHER PUBLICATIONS

European Patent Office, Communication Pursuant to Article 94(3) EPC in European Patent Application No. 10 766 876.6 (Oct. 2, 2013).
(Continued)

*Primary Examiner* — Jill Warden
*Assistant Examiner* — Brittany Fisher
(74) *Attorney, Agent, or Firm* — Leydig, Voit & Mayer, Ltd.

(57) ABSTRACT

Provided are a jig for uniformly applying a drug liquid to a microneedle, and a method of applying a drug to a microneedle using same. Grooves of a number corresponding to the number of rows of small needles of a microneedle are formed in the surface of a flat plate jig or of a roller-like jig, and a drug liquid is filled and held in the grooves. The drug liquid is applied to the microneedle by inserting the small needles of the microneedle into the surface of the drug liquid held in the narrow grooves, and immersing the small needles in the drug liquid. By this, the drug liquid is uniformly applied to the small needles of the microneedle without unevenness between the central section and the peripheral section of each microneedle, and thus the microneedles having good quality can be easily manufactured.

10 Claims, 12 Drawing Sheets

(51) Int. Cl.
*A61M 37/00* (2006.01)
*A61K 9/00* (2006.01)

(56) References Cited

U.S. PATENT DOCUMENTS

| | | |
|---|---|---|
| 2003/0221965 A1 | 12/2003 | Seino et al. |
| 2004/0028875 A1* | 2/2004 | Van Rijn et al. ............... 428/98 |
| 2004/0049150 A1 | 3/2004 | Dalton et al. |
| 2005/0084604 A1 | 4/2005 | Trautman et al. |
| 2007/0009587 A1 | 1/2007 | Daddona et al. |
| 2007/0293816 A1* | 12/2007 | Chan et al. ..................... 604/46 |
| 2008/0051699 A1* | 2/2008 | Choi et al. ..................... 604/46 |
| 2008/0262444 A1 | 10/2008 | Takada |
| 2009/0143749 A1* | 6/2009 | Sugimura et al. ............. 604/272 |
| 2010/0004608 A1 | 1/2010 | Hamamoto et al. |
| 2011/0046575 A1 | 2/2011 | Takada |

FOREIGN PATENT DOCUMENTS

| | | |
|---|---|---|
| JP | H04-047862 U1 | 4/1992 |
| JP | 2002-239014 A | 8/2002 |
| JP | 2003-344357 A | 12/2003 |
| JP | 2004-504120 A | 2/2004 |
| JP | 2008-546483 A | 12/2008 |
| WO | WO 01/73396 A1 | 10/2001 |
| WO | WO 02/07813 A1 | 1/2002 |
| WO | WO 2006/080508 A1 | 8/2006 |
| WO | WO 2006/138719 A2 | 12/2006 |
| WO | WO 2007/002123 A3 | 1/2007 |
| WO | WO 2008/093679 A1 | 8/2008 |

OTHER PUBLICATIONS

Ameri et al., *Pharmaceutical Research*, 27(2): 303-313 (2010).
Japanese Patent Office, International Search Report in International Patent Application No. PCT/JP2010/002967 (May 25, 2010), English translation.
Japanese Patent Office, Written Opinion in International Patent Application No. PCT/JP2010/002967 (May 25, 2010), English translation.
European Patent Office, Extended European Search Report in European Application No. 10766876.6 (Jul. 25, 2012).

* cited by examiner

Needles are lowered by micro-positioner, while observing through digital microscope, and immersed in antigen solution a) Drug liquid plate Top view b)

Side view

Cross sectional view
(cut along A)

Cross sectional side view

MEDICATION LIQUID SUPPORTING JIG AND METHOD OF APPLYING MEDICATION TO MICRO-NEEDLE USING SAME

TECHNICAL FIELD

The present invention relates to a method of uniformly applying a drug to a microneedle, and a jig used for the method of application.

BACKGROUND ART

As a method of administering a drug transdermally by the use of a microneedle, there is a method, as disclosed in Patent Document 1, of kneading a drug into a material of a microneedle and then processing the resultant into a microneedle. On the other hand, Patent Document 2 describes a method of coating a drug on the surface of a microneedle by the medium of sugar.

In manufacturing a microneedle, since the material is often subjected to a process of change in shape by heating, thermally unstable drugs cannot be mixed into the material. In particular, for proteins, antibodies, vaccines, and the like, since they are thermally unstable, methods of manufacturing the microneedle are limited and difficult to be applied to mass production.

On the other hand, a method of applying a drug to a premade microneedle is generally a method, as disclosed in Patent Document 2, of immersing a microneedle in a solution in which a drug is dissolved. However, there is a difficulty to efficiently apply the drug to only small needles of the microneedle. Specifically, in order to uniformly immerse only the small needles of the microneedle in the drug liquid, a large drug liquid tank is required so as to level the surface of the drug liquid with respect to the small needles. When the drug liquid tank is large, the liquid surface is likely to be shaken due to vibration or wind. Therefore, the drug adheres to a base plate part of the small needles, resulting in uneven adhesion of the drug. The increase in size of the drug liquid tank requires a great amount of drug to be used, and therefore this is not realistic for expensive proteins. Conversely, when the drug liquid tank is small, as shown in FIG. 1, the liquid surface is convex due to surface tension; therefore, when the small needles are immersed therein, the immersed area of the small needles is different between the center part and the peripheral part of the tank. Moreover, when the drug liquid is an aqueous solution, the effect of surface tension is especially high. Thus, it is observed that, even though the drug liquid can be applied to the small needles in the center part, it cannot be sufficiently applied to the small needles in the peripheral part.

While a wide variety of methods of manufacturing a microneedle have been studied and reported, a method of applying a drug liquid to a premade microneedle has been rarely reported. Furthermore, a method of application which can be industrially mass-produced in a realistic way has not been reported, and various methods are still now under research and study.

Patent Document 1: WO2006/080508
Patent Document 2: JP 2004-504120A

DISCLOSURE OF THE INVENTION

Problems to be Solved by the Invention

An object of the present invention is to provide a method of uniformly applying a drug to small needles of a microneedle, and a jig used for the method.

Means for Solving the Problems

The present inventors have made intensive investigations in order to solve the above problems. For example, they have studied various methods of applying an antigen solution as a drug to a microneedle. Specifically, as a method that can be applied to mass production, the present inventors have selected and examined a method of immersing a microneedle in an antigen solution tank. Then, the following problems have clearly appeared: a) shaking of the entire device and b) shaking of the horizontal surface and securement of flatness in the antigen solution.

In particular, b) has been problematic. When a small amount of solution having a high concentration of antigen is used and applied to small needles of a microneedle, there is a problem of surface tension as shown in FIG. 1, and thus it is difficult to apply the drug liquid uniformly. On the other hand, when the amount of the solution used is increased so as to secure the horizontal surface, this requires a great amount of drug and increases the cost. Thus, the antigen concentration should be lowered. In that case, in order to allow a necessary amount of drug to be carried thereon, small needles need to be immersed in the solution many times.

Moreover, when the solution surface is enlarged so as to secure the horizontal surface, the surface is likely to be affected by shaking of the device or wind. When the location of the small needles to be immersed is moved too close to the liquid surface accidentally, the effects described above cause the liquid surface to contact with the base of the microneedle. Then, the drug liquid adheres all over the microneedle due to surface tension, which makes it impossible to uniformly apply the drug to the small needles.

Here, instead of immersing the small needles of the microneedle in a single solution tank at once, the present inventors have conceived the idea of using individual solution tanks (drug liquid holding grooves) corresponding to the small needles. It is found out that, when grooves are made in the solution tank as shown in FIGS. 2 to 4 to fix the liquid surface inside the narrow grooves, the effects of shaking of the device and wind can be eliminated. Furthermore, it is found out that, since the liquid surface is fixed inside the narrow grooves, it is less likely to be affected by a slight inclination of the device.

As shown in FIG. 5, there is prepared a flat plate having one drug liquid holding groove whose cross sectional shape is a semicircle. When a drug liquid is filled thereinto excessively, it is raised in a convex manner due to surface tension. Even though the liquid surface is convex like this, since it is fixed due to surface tension, it is less likely to be affected by external environment such as wind. As shown in FIGS. 6 to 9, when grooves are made to fit the pitch distance between small needles of a microneedle and all grooves communicate with one another, each groove has the liquid surface of the same height. Moreover, since the liquid surface is flat or convex, it is easy to immerse only the small needle part. As a result, it is found out that an extra wet part to other parts (base of a microneedle) is lessened. Furthermore, since the drug liquid is poured only into the groove part, the amount of the drug liquid used is economical, thereby the amount of the drug (antigen) used can be reduced.

Furthermore, as shown in FIG. 15, a roll having a plurality of drug liquid holding grooves is prepared. Then, the lower part of the roll is immersed in a drug liquid tank and rotated. The drug liquid that has adhered to the roll surface is wiped off with a plate-like tool so that the drug liquid is carried only in the drug liquid holding grooves. Then, a microneedle is set such that small needles of the microneedle can be immersed in the drug liquid holding grooves in the upper part of the roll, and thereby the small needles can pass through the drug liquid holding grooves in the upper part of the roll. The passing of the small needles through the drug liquid holding grooves allows the drug liquid to adhere only to the surface of the small needles. The microneedle to which the drug liquid has adhered can be dried during the transfer thereof. In this way, it is possible to apply the drug liquid to the microneedle successively and allow the microneedle to pass through the upper part of the roll multiple times, depending on a necessary amount to be applied.

As described above, the method of the present invention makes it possible to immerse only small needles of a microneedle easily and repeatedly, and thereby appropriately manufacture a microneedle to which a desired amount of drug is provided.

Moreover, the present invention makes it possible, to not only use one flat plate jig for applying a drug liquid to one microneedle, but also to use a plurality of microneedles as a set and apply a drug liquid to the plurality of microneedles simultaneously, for example, by lengthening grooves that hold a drug liquid (drug liquid holding grooves) or increasing the number of the drug liquid holding grooves.

With the above findings, a jig and a method for effectively applying a drug to a microneedle have been found, and thus the present invention has been completed.

A summary of the present invention is as follows.

[1] A jig for allowing small needles to carry a drug liquid, the jig being a flat plate having one or more drug liquid holding grooves and being used for allowing small needles of a microneedle to carry a drug liquid, wherein
   a) a pitch distance between the grooves is 300 to 1000 µm;
   b) a width of each groove is 100 to 700 µm; and
   c) a depth of each groove is 100 to 700 µm.

[2] The jig according to [1], wherein the number of the drug liquid holding grooves is plural, and both ends of each groove reach both ends of the flat plate.

[3] The jig according to [1], wherein the number of the drug liquid holding grooves is plural, both ends of each groove do not reach both ends of the flat plate, and the grooves are connected to one another at one end or both ends of each groove by the use of other groove(s) as required in order to level the ridge height of the liquid surface, which is convex, of each groove.

[4] The jig according to any one of [1] to [3], wherein the flat plate is made of silicon.

[5] The jig according to any one of [1] to [4], wherein the flat plate has a quadrangular shape of 1 to 5 cm long and 1 to 5 cm wide.

[6] The jig according to any one of [1] to [5], wherein the drug liquid holding groove has a cross sectional shape of an inverted triangle, a quadrangle, or a semicircle.

[7] A method of carrying a drug on small needles of a microneedle, comprising using the jig according to any one of [1] to [6], and comprising the following steps (1) to (5):
   (1) placing the flat plate jig horizontally;
   (2) pouring a drug liquid onto the surface of the flat plate jig to fill the drug liquid holding groove(s) with the drug liquid;
   (3) wiping off an excess amount of the drug liquid remaining on the surface of the flat plate jig;
   (4) immersing small needles of the microneedle into the drug liquid in the groove(s); and
   (5) pulling up the immersed small needles and drying them to manufacture the microneedle carrying the drug.

[8] The method according to [7], wherein the drug liquid is applied to the small needles multiple times to provide a predetermined amount of the drug on the microneedle.

[9] A method of carrying a drug on small needles of a microneedle, comprising using the jig according to any one of [1] to [6], and comprising the following steps (1) to (5):
   (1) placing the flat plate jig horizontally;
   (2) pouring a drug liquid to be applied into the groove(s), and allowing the liquid surface to be convex due to surface tension so that the convex liquid surface is protruded from the surface of the flat plate jig;
   (3) adjusting small needles of the microneedle such that the small needles are inserted into the ridge of the convex liquid surface;
   (4) lowering a plate on which the microneedle are placed, inserting the small needles into the ridge of the convex liquid surface, and immersing the small needles in the drug liquid; and
   (5) pulling up and drying the immersed small needles to manufacture the microneedle to which the drug is applied.

[10] The method according to [9], comprising using the jig according to claim 3.

[11] The method according to [9] or [10], wherein the drug liquid is applied to the small needles multiple times to provide a predetermined amount of the drug to the microneedle.

[12] A flat plate jig, having a quadrangular shape of 1 to 5 cm long and 1 to 5 cm wide, and comprising the following groove(s) of (1) to (4):
   (1) one or more linear grooves;
   (2) a pitch distance between the grooves is 300 to 1000 µm;
   (3) a width of each groove is 100 to 700 µm; and
   (4) a depth of each groove is 100 to 700 µm.

[13] The flat plate jig according to [12], wherein the number of the grooves is plural, and both ends of each groove reach both ends of the flat plate.

[14] The flat plate jig according to [12], wherein the number of the grooves is plural, both ends of each groove do not reach both ends of the flat plate, and the grooves are connected to one another at one end or both ends of each groove by the use of other groove(s) as required in order to level the ridge height of the liquid surface, which is convex, of each groove.

[15] The flat plate jig according to any one of [12] to [14], wherein the flat plate is made of silicon.

[16] The flat plate jig according to any one of [12] to [15], wherein the groove has a cross sectional shape of an inverted triangle, a quadrangle, or a semicircle.

[17] A flat plate jig having a quadrangular shape of 1 to 5 cm long and 1 to 5 cm wide and including a photosensitive resist film of 100 to 500 µm thickness on a flat plate,
   wherein a part of the photosensitive resist film corresponding to the following groove(s) of (1) to (5) is removed,
   (1) one or more linear grooves;
   (2) a pitch distance between the grooves is 300 to 1000 µm;
   (3) a width of each groove is 100 to 700 µm;
   (4) a depth of each groove is 100 to 700 µm; and
   (5) the grooves are connected to one another at one end or both ends of each groove by the use of other groove(s) where necessary in order to level the ridge height of the liquid surface, which is convex, of each groove.

[18] The flat plate jig according to [17], wherein the surface of the photosensitive resist film is coated with a hydrophobic material.

[19] The flat plate jig according to [17] or [18], wherein the flat plate is made of silicon.

[20] The flat plate jig according to any one of [17] to [19], wherein the drug liquid holding groove has a cross sectional shape of an inverted triangle, a quadrangle, or a semicircle.

[21] A jig for allowing small needles to carry a drug liquid, the jig having a roll-like shape with one or more drug liquid holding grooves and being used for allowing small needles of a microneedle to carry the drug liquid, wherein
a) a pitch distance between the grooves is 300 to 1000 µm;
b) a width of each groove is 100 to 700 µm; and
c) a depth of each groove is 100 to 700 µm.

[22] The roll-like jig according to [21], wherein the surface of the roll-like jig is coated with a hydrophobic material.

[23] The roll-like jig according to [21] or [22], wherein the roll-like jig is made of silicon.

[24] The roll-like jig according to any one of [21] to [23], wherein the drug liquid holding groove has a cross sectional shape of an inverted triangle, a quadrangle, or a semicircle.

[25] A method of carrying a drug liquid on small needles of a microneedle, comprising using the roll-like jig according to any one of [21] to [24].

Effects of the Invention

According to the jig for carrying a drug liquid of the present invention and the method of applying a drug by using the jig, the manufacture of a flat plate jig having an appropriate drug liquid holding groove(s) makes it possible to apply a drug to small needles of a microneedle in various shapes economically and effectively. Moreover, it is easy to manufacture a microneedle to which a necessary amount of drug is applied, by immersing the small needles with this jig repeatedly.

EMBODIMENTS FOR CARRYING OUT THE INVENTION

Figure 1:
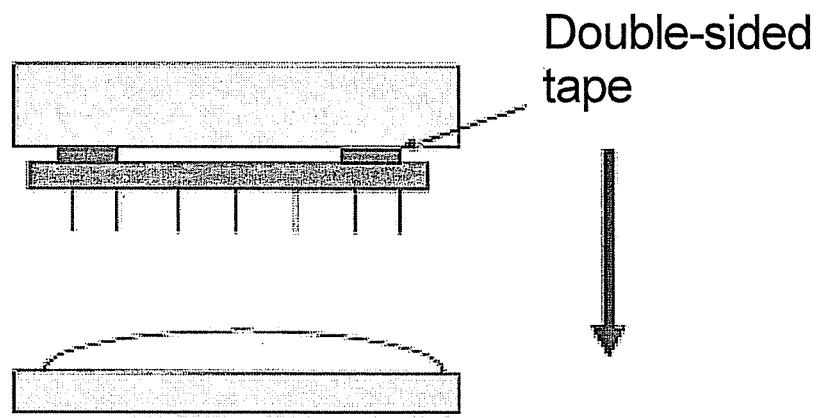
FIG. 1 is a schematic diagram showing a problem of immersion and application of small needles in a conventional method (a drug liquid in a single tank), i.e., effects of the curved liquid surface of the drug liquid.
Figure 2:
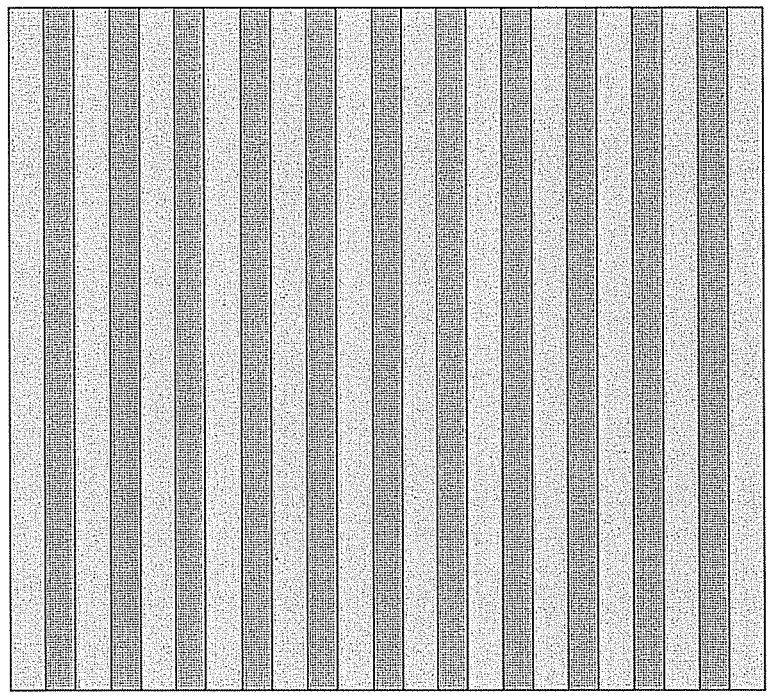
FIG. 2 includes views (a top view and a side view) showing one example of a flat plate jig (a drug liquid plate) including the drug liquid holding grooves of the present invention.
Figure 2:
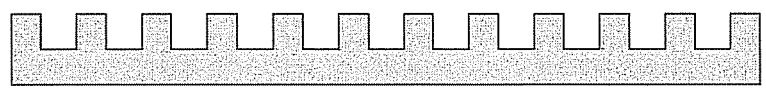

The "microneedle" as used herein refers to a pin-frog-shaped (kenzan-shaped) plate, on which 9 to 500 small needles described as follows are placed,
a) the height of the small needles is 150 µm to 1 mm;
b) the maximum diameter of the base of the small needles is 50 µm to 500 µm;
c) the interval distance (pitch) between the small needles is 300 µm to 1 mm, and
e) the small needles are aligned in 3 to 30 horizontal rows and 3 to 30 vertical rows.

When the height of the small needles is small, it is difficult to apply a drug liquid thereto; therefore the height of the small needles is preferably 200 µm or more. More preferably, the height of the small needles is in the range of 300 to 500 µm. The microneedle of the present invention can be manufactured by known methods, and may be manufactured according to the method disclosed in WO2008/093679.

The size of the microneedle of the present invention is 0.5 to 1.5 cm long and wide. The number of the small needles and the size of the microneedle may be selected appropriately as required. The material of the microneedle of the present invention may be a metal or a biodegradable resin. Examples of the metal include Ni, NiFe, Ti, Pd, Au and Cu, and a preferable example thereof is Ni. The biodegradable resin is not particularly limited as long as it is a resin including a component that is degraded and absorbed in the body. Examples of the biodegradable resin include aliphatic polyesters, such as polylactic acid, polyglycolic acid, and a copolymer of lactic acid and glycolic acid; and sugars, such as maltose, lactose, sucrose, mannitol, and sorbitol. As aliphatic polyesters, polylactic acid or polyglycolic acid is preferably used. As polysaccharides, maltose is suitably used. Polylactic acid with desired properties may be obtained by being mixed with esters of lactic acid such as methyl lactate, butyl lactate, and hexadecyl lactate, or with common additives such as a thermal stabilizer, a stabilization aid, a plasticizer, an antioxidant, a light stabilizer, a flame retardant, and a lubricant, which are used for stabilization and modification of plastic resins.

The "flat plate jig" as used herein refers to a jig made of silicon (Si), metal, PMDS (polydimethylsiloxane), or the like, in which one or more grooves are provided on the flat plate surface. It also refers to a jig manufactured by coating a photosensitive resist such as a UV curing resin on a silicon substrate and removing a part that has not been exposed, to be used as groove(s). Any size of the jig is employed as long as the jig ensures the necessary size of the groove(s) in order to immerse the small needles of the microneedle.

The metal used in the jig refers to the same material as described above. The PDMS refers to a resin obtained by polymerizing and curing dimethyl siloxane oligomers with a catalyst and the like, and a commercially available PDMS may be used. The UV curing resin refers to a resin composed of a monomer, an oligomer, a photoinitiator, and an additive. General-purpose UV curing resins which are commercially available may be used.

The "roll-like jig" as used herein refers to a jig made of silicon (Si), metal, or the like, in which one or more grooves are provided on the roll-like surface. For example, materials for a roll used in gravure printing may be used.

The "groove" as used herein refers to a groove having a cross sectional shape of an inverted triangle, a semicircle, or a quadrangle, and the shape of the groove is as described below,
   a) one or more linear grooves;
   b) the pitch distance between the grooves is 300 to 1000 μm;
   c) the width of each groove is 100 to 700 μm; and
   d) the depth of each groove is 100 to 700 μm.

For the groove, there are two cases, where both ends of each groove reach both ends (side walls) of the flat plate and thus they are open ended, and where the groove does not reach both ends (side walls) of the flat plate and thus they are located within the flat plate. When the number of the grooves is plural, it may be possible to connect the plurality of grooves with one or more transverse grooves, in order to supply a drug liquid to the grooves smoothly and level the surface of the drug liquid in the grooves.

Alternatively, it may be possible to connect the grooves at one end or both ends of each groove with a transverse groove (s), in order to supply a drug liquid to each groove smoothly and level the surface of the drug liquid or in order to level the height of ridge of a drug liquid in each groove when the drug liquid is supplied excessively so that the liquid surface in the groove is convex.

Figure 8:
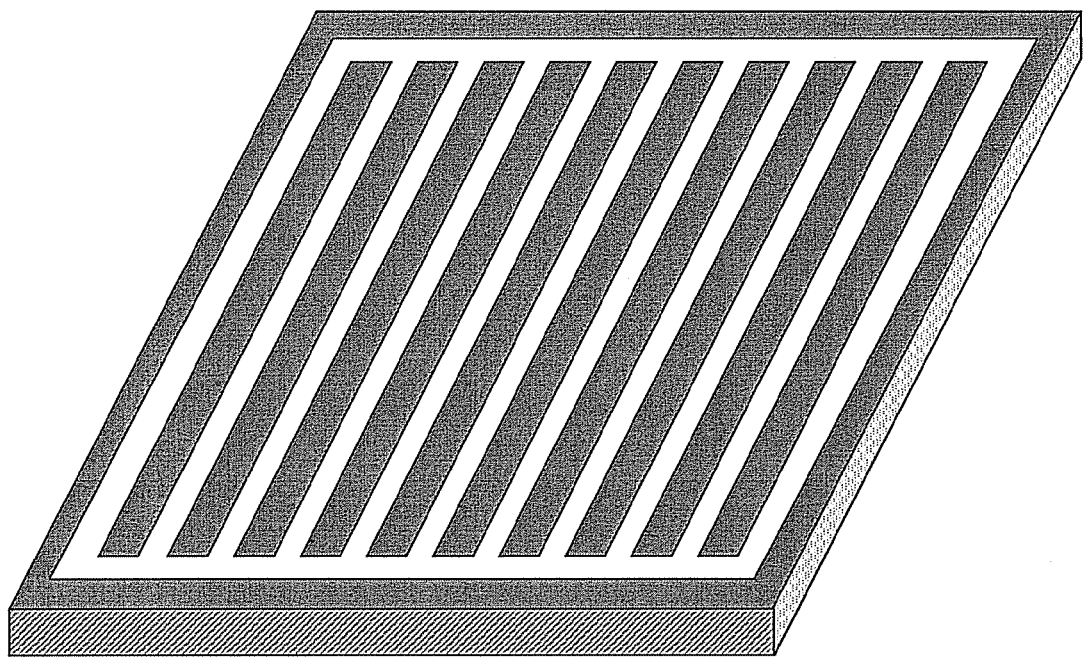
FIG. 8 includes views (an entire perspective view and a cross sectional view) showing one example of a flat plate jig, in which etching has been done in a comb-like pattern (white part) on a flat plate to be used as drug liquid holding grooves, and the black part is the surface of the flat plate jig.
Figure 8:
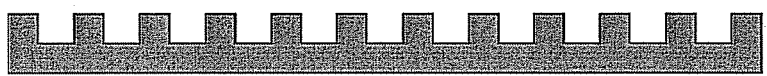
Figure 10:
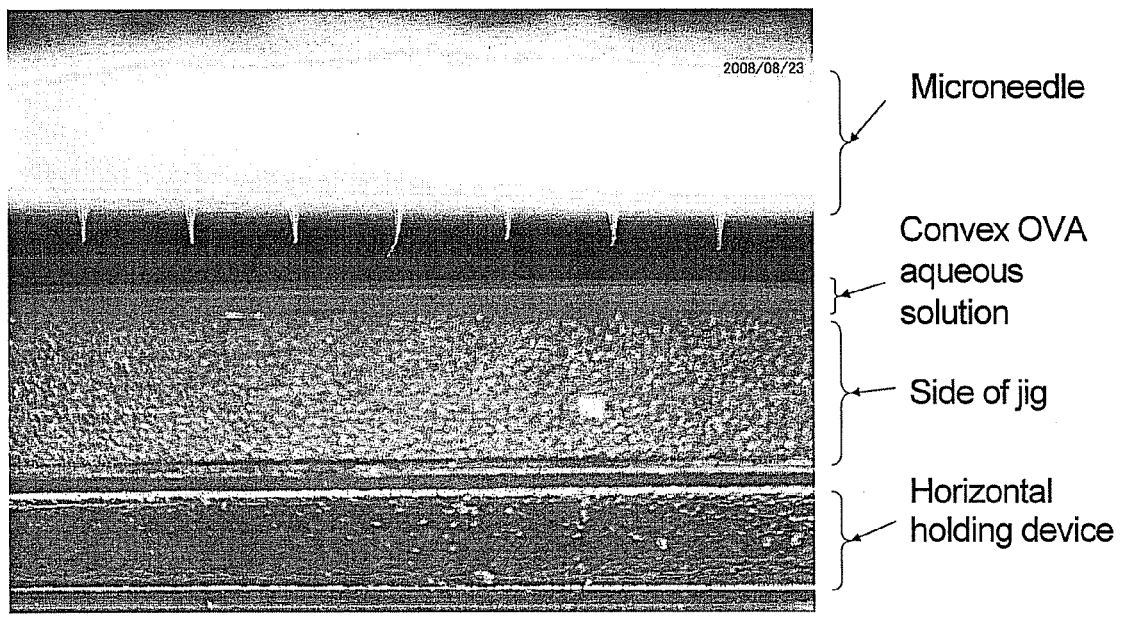
FIG. 10 is a side view (a magnified photograph) showing the state of a device in which the following steps are set: placing the jig of the present invention illustrated in FIG. 5 on a horizontal holding device; supplying a drug liquid to the drug liquid holding groove to allow the liquid surface to be raised in a convex manner; and thereafter inserting a microneedle into the ridge of the convex liquid surface.

The grooves in the present invention are specifically shown in, for example, FIGS. 8 and 10. That is, the grooves are formed on a flat plate made of silicon (Si) by semiconductor processes and the like. In the semiconductor processes used in the present invention, various known methods as well as known fine fabrication processes used for manufacturing small needles may be used appropriately. Examples thereof include lithography, sputtering, and electroplating. These techniques are described in commonly used books and may be performed with reference to or according to, for example, "Nanoprinting technique for beginners" by Jun Taniguchi (Kogyo Chosakai Publishing Co., Ltd., 2005), "Silicon Micromachining" by M. Elwenspoek (Springer-Verlag Tokyo, Inc., 2011), "Introduction to Microelectronic Fabrication" by Jaeger (Addison-Wesley Publishing Co., Reading Mass. 1988), "Semiconductor Integrated Circuit Processing Technology" by Runyan et al., (Addison-Wesley Publishing Co., Reading Mass. 1990), "Proceedings of the IEEE Micro Electro Mechanical Systems Conference 1987-1998", "Handbook of Microlithography, Micromachining & Microfabrication" edited by Rai-Choudhury (SSPIE Optional Engineering Press, Bellingham, Wash. 1997). The means of manufacturing the jig refer to a general means used in the semiconductor manufacturing processes or the fine fabrication processes described above, and examples thereof include lithography such as X-ray lithography and photolithography; and etching such as ion etching and plasma etching. A preferable example thereof is inductively coupled plasma reactive ion etching (abbreviated as ICP-RIE).

The "drug liquid" as used herein refers to a solution in which a drug to be applied is dissolved, or a dispersion in which the drug is uniformly dispersed. An aqueous solution or an organic solvent solution may be used depending on the solubility of the drug to be applied. The drug to be applied is not particularly limited as long as it has been used for treatment so far. When the drug is a biological polymer such as a protein, an antigen, or an antibody, since the polymer has high solubility in water, an aqueous solution is used as the drug liquid. When the drug is a low molecular compound such as an antibiotic or an antipsychotic drug, an aqueous solution or an organic solvent solution may be used depending on the solubility thereof.

Figure 3:
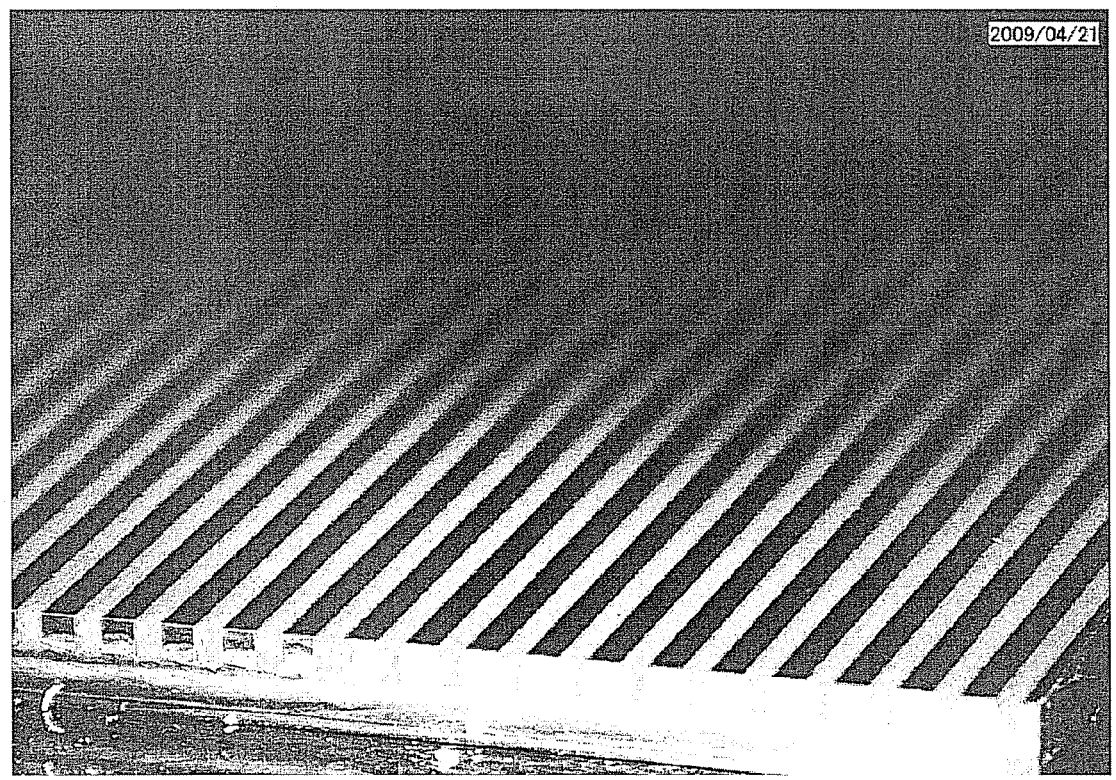
FIG. 3 is a perspective view (a magnified photograph) showing the state of a flat plate jig after the following steps of: supplying a yellow aqueous solution containing a fluorescent dye (carboxyfluorescein) to the flat plate jig of the present invention, in which both ends of drug liquid holding grooves reach both side walls of the flat plate jig and thus they are open ended; filling the drug liquid holding grooves with the yellow aqueous solution; and removing the yellow aqueous solution remaining on the surface of the flat plate jig.
Figure 4:
FIG. 4 is a side view (a magnified photograph) of the flat plate jig of FIG. 3.

In pouring the drug liquid, the amount of drug liquid is set such that the liquid surface of each groove will be level in height. Then, the drug liquid is supplied to the surface of the flat plate jig or to the groove. For example, the drug liquid is supplied to the surface of the flat plate jig of the present invention and to fill each groove. Thereafter, the surface is leveled with a brush or the like so that extra drug liquid does not remain on the surface of the flat plate jig as shown in FIG. 3. When this state is observed from the side of grooves, as shown in FIG. 4, it is found out that a yellow drug liquid is filled in each groove, and each liquid surface of the drug liquid is horizontal and located at the same position as the surface of the flat plate jig. As seen from the above, since the liquid surface inside the narrow groove is likely to be fixed due to surface tension, the effects of wind and vibration can be suppressed. Furthermore, since the height of the liquid surface in each groove is the same, there is no difference of the liquid surface between the center part and the both ends of the groove. As a result, by immersing small needles of a microneedle into the grooves and applying a drug liquid to the small needles, it is possible to overcome the non-uniformity of application (variation of applied area of small needles) resulting from the shaking of the liquid surface, which is apt to be generated in the case of using a single drug solution tank.

Figure 5:
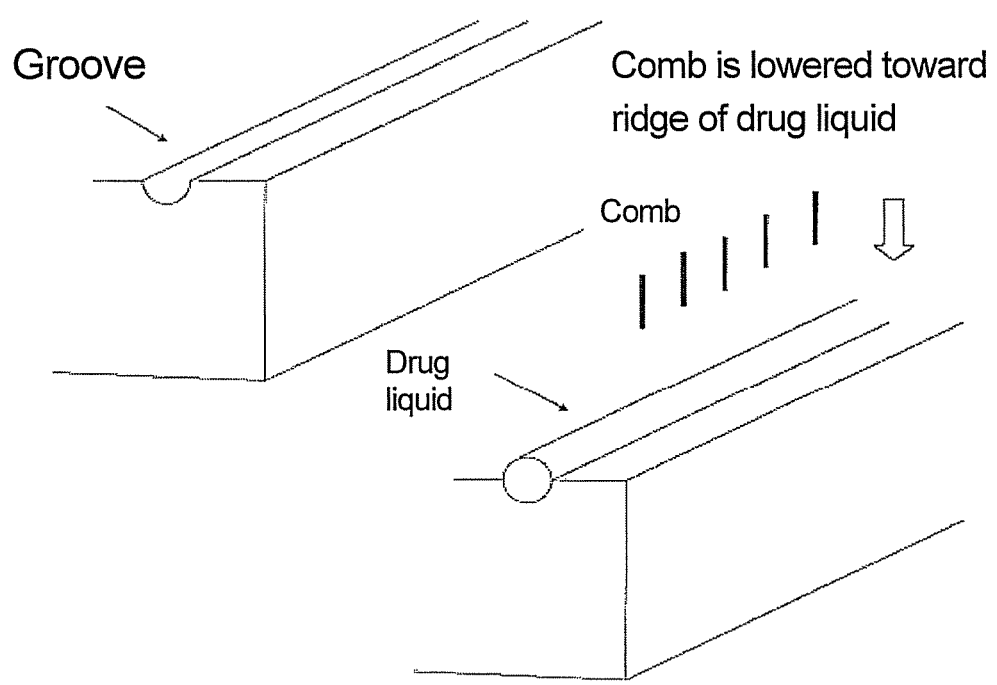
FIG. 5 is a schematic diagram showing the state when excessively supplying a drug liquid to a drug liquid holding groove, allowing the liquid surface to be raised in a convex manner due to surface tension, inserting and immersing a microneedle into the ridge of the convex liquid surface, and applying the drug liquid to small needles.
Figure 9:
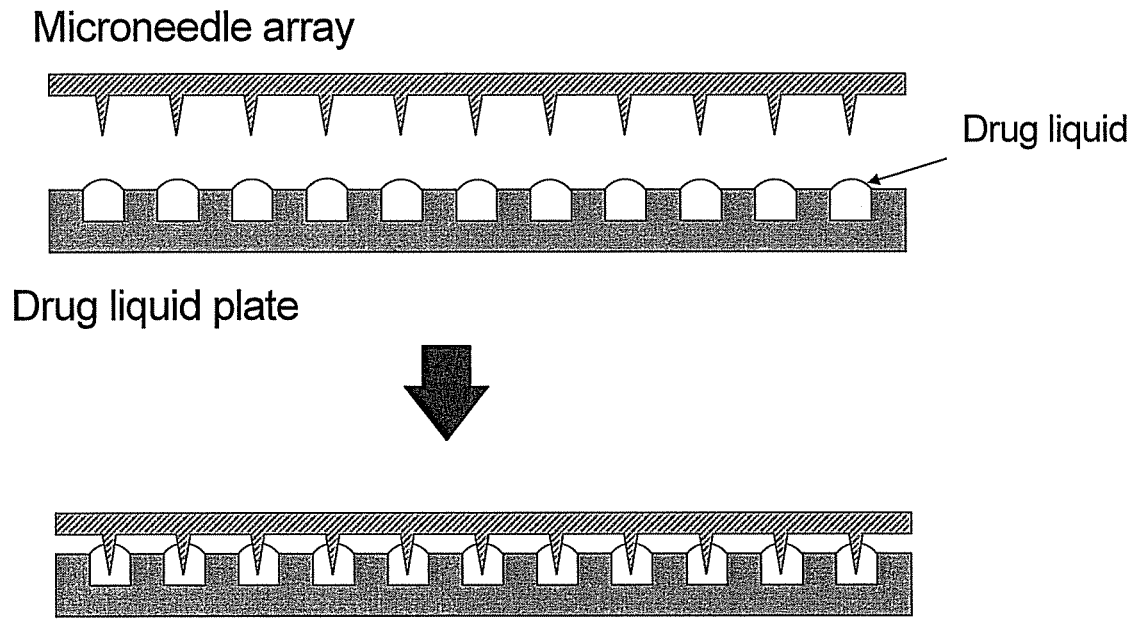
FIG. 9 is a schematic diagram showing the state when supplying a drug liquid to the drug liquid holding grooves (white part) illustrated in FIG. 8, allowing the liquid surface to be raised in a convex manner, and thereafter inserting and immersing a microneedle into the ridge of the convex liquid surface.
Figure 11:
FIG. 11 is a side view (a magnified photograph) showing the state when operating the device illustrated in FIG. 10 and immersing the microneedle in the drug liquid holding groove.

For example, to fill the grooves, in the case of pouring drug liquid into a part of the grooves or a solution reservoir or the like connected to the grooves, when there is a transverse groove for communication, all grooves communicate with one another and thus the height of the liquid surface is the same. It may be possible to pour the drug liquid additionally so that the liquid surface is raised in a convex manner due to surface tension as shown in FIGS. 5 and 9. At this time, the peak (ridge) of the convex liquid surface is protruded upward from the horizontal surface of the flat plate as shown in FIG. 10. When the convex liquid surface is formed due to surface tension as described above, the effects of wind and vibration can be suppressed, in the same manner as in leveling the surface of the flat plate jig by the use of a brush or the like. Moreover, it is possible to level the height of the liquid surface in each groove and practically ignore the difference of the liquid surface between the center part and the both ends of the groove, which results in that each small needle of the microneedle can be immersed at the same depth, as shown in FIG. 11.

In the case that the number of the transverse grooves for communication is large, for example, when the transverse grooves are provided in a grid pattern or the like, it is possible to achieve the object in the same manner as in FIG. 8. Moreover, even when the liquid surface in the drug liquid holding groove is not protruded in a convex manner or when it is concave, it is possible to apply the drug liquid to the small needles, without being affected so much by the shape of the liquid surface. For immersion of the small needles, when the small needles are immersed into a certain depth thereof, it is seen that the liquid surface of the drug liquid travels along the small needles at one time to wet a base of the microneedle with the drug liquid. Specifically, as shown in FIG. 11, when the small needles are immersed, the liquid surface around the small needles is attracted towards the small needles so that the liquid surface between the small needles is curved. The reason may be high wettability of the material of the small needles against water. When the material of the small needles is likely to be wet with water, an aqueous solution travels along the small needles to wet the base of the microneedle. When the material of the small needles is a polyester resin such as polylactic acid or polyglycolic acid, since it has good wettability, it is considered that an aqueous solution likely travels and moves upward along the small needles. On the other hand, when the drug liquid holding groove is narrow in width, surface tension functions between the side walls of the groove and the aqueous solution, and thus it is possible to suppress the tendency in which the aqueous solution travels and moves upward along the small needle. Therefore, the width of the groove that is required to suppress the force of the aqueous solution for traveling along the small needles is preferably 0.7 mm or less.

Moreover, in order to suppress the moving upward of the aqueous solution along the small needles, it is considered to be preferable to have the state in which the liquid surface around the small needles is divided into small sections, or the small needle is surrounded by 4 or more protrusions.

Figure 14:
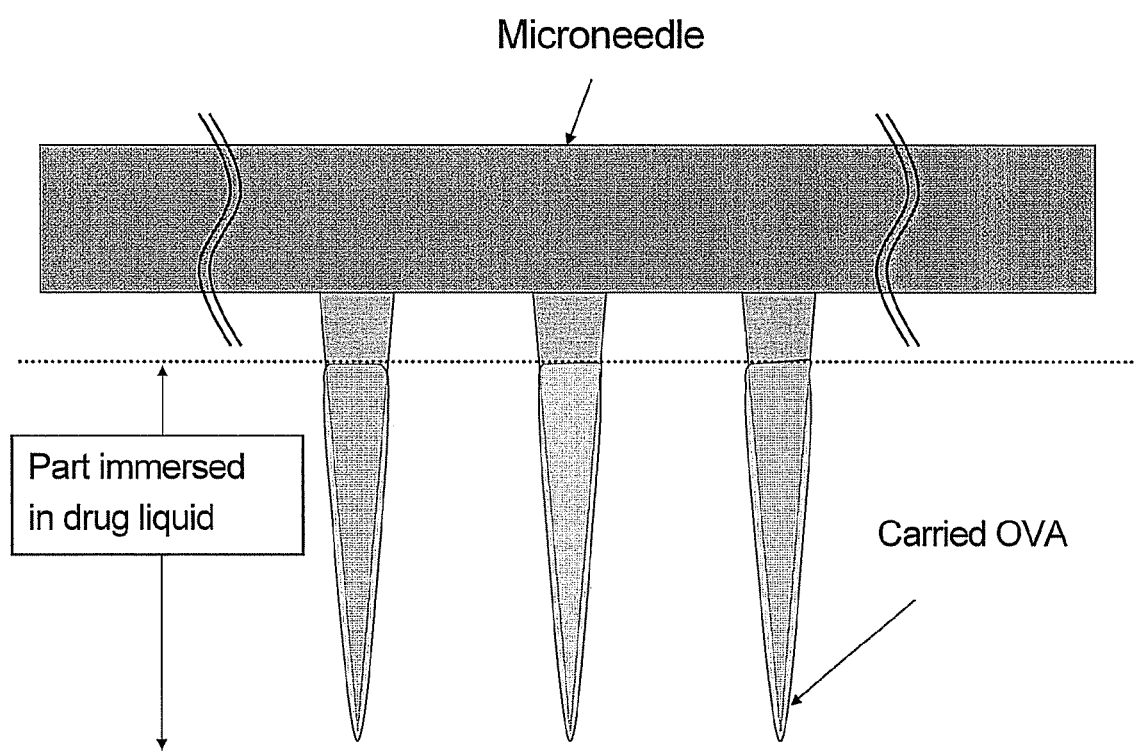
FIG. 14 is a schematic diagram (a side view) showing that immersing small needles of a microneedle in an aqueous OVA solution achieves uniform application of OVA.

In order to allow the small needles of the microneedle to carry the drug (application), it is necessary, as described above, to immerse the small needles in the liquid surface of the drug liquid that has been filled in the groove (drug liquid holding groove) of the flat plate jig of the present invention, and dry the resultant small needles. Accordingly, there is manufactured a microneedle to which a drug is applied as shown in FIG. 14. Here, the amount of the drug applied to the small needles of the microneedle can be confirmed and quantified by re-elution of the adhered drug by known methods, for example, in the case of proteins, such as an ELIZA method or a colorimetric method. Alternatively, it can be quantified indirectly by allowing a fluorescent dye to coexist and re-eluting the adhered fluorescent dye. Moreover, when a desired amount of drug is required, it is possible to repeat immersing and drying the small needles until the desired amount to be applied is attained.

The "photosensitive resist film" as used herein refers to a film of a resin that cures in response to light such as UV (UV curing resin) or a resin film that reacts with light and can be removed therefrom. Examples of the UV curing resin include general-purpose UV curing resins which are commercially available and composed of a monomer, an oligomer, a photoinitiator, and an additive. Examples of the resin film that reacts with light and can be removed therefrom include PMER. Preferable examples thereof include P-HM3000PM (manufactured by TOKYO OHKA KOGYO CO., LTD.) and P-LA900PM (manufactured by TOKYO OHKA KOGYO CO., LTD.).

Figure 6:
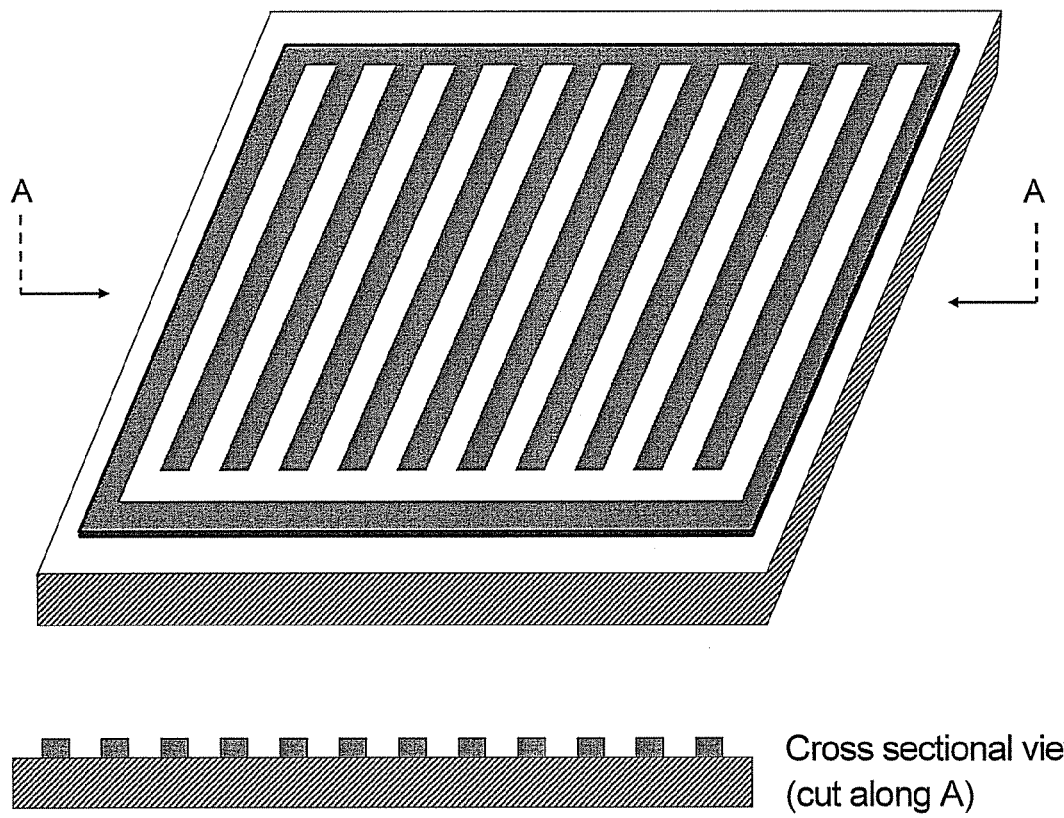
FIG. 6 includes views (an entire perspective view and a cross sectional view) showing one example of the flat plate jig of the present invention, in which a hydrophobic material (black part) is drawn in a comb-like pattern on a flat plate, and the other part (white part) is the surface of the flat plate.

It is possible to apply and coat the photosensitive resist film on a flat plate made of silicon or metal, overlay a drawing pattern having a desired shape of groove, and irradiate the resultant with UV to cure or remove the necessary resin part, and thereby manufacture a flat plate jig as shown in FIG. 6.

The "hydrophobic material" as used herein refers to a material having a property of repelling water easily and used, when a drug liquid in which a drug is dissolved forms the convex liquid surface, for preventing the drug liquid from being mixed together across the photosensitive resist film. Specifically, examples thereof include viscous fats and oils, and Teflon (registered trademark).

Figure 15:
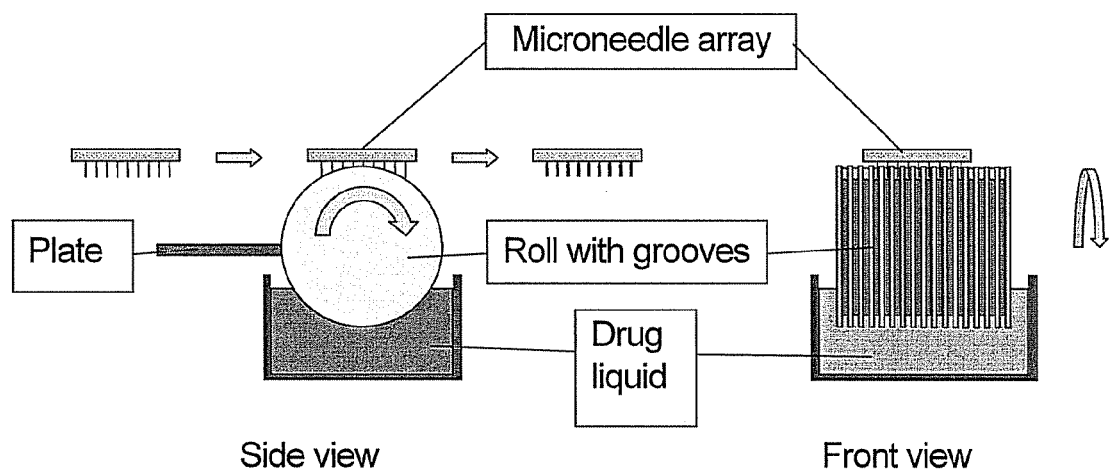
FIG. 15 is a schematic diagram showing a method of allowing small needles of a microneedle to carry a drug liquid by using a roll-like jig for carrying a drug liquid.

The "method for carrying a drug liquid" or "method of allowing small needles of a microneedle to carry a drug liquid" as used herein refers to a method of applying a drug liquid to only small needles of a microneedle and allowing the small needles to carry the drug liquid by using the "flat plate jig" or the "roll-like jig" of the present invention. Specifically, this is a method of immersing the small needles of the microneedle in the drug liquid that has been held in the jig having one or more drug liquid holding grooves, in order for application of the drug solution. A plate for intaglio printing or a roll-like plate for gravure printing may be used as the jig. For example, a method of carrying a drug liquid by using the roll-like jig is as follows. As shown in FIG. 15, when a roll rotates in the same manner as in gravure printing, the drug liquid hangs on the roll and moves upward. Then, the drug liquid that excessively adheres thereto is wiped off with a plate so that the drug liquid remains only in the drug liquid holding grooves. After that, small needle part of the microneedle that has been parallel-transferred are immersed into the drug liquid holding grooves so that the drug liquid is applied to the needle part of the microneedle array. Other than the drug liquid holding grooves placed on the roll, a recessed area may be used as the drug liquid reservoir.

The method of carrying a drug liquid by using the roll-like jig is a system that can achieve successive application and relatively easy and simple operation control. Moreover, the method can use a drug liquid economically and effectively, and therefore it is very useful as a method of applying a drug liquid to a great number of microneedles successively.

EXAMPLES

The present invention will be described specifically with reference to examples; however, it is not limited to any of the following examples.

Example 1

Application of Drug Liquid to Small Needles of Microneedle

A microneedle having 10 small needles in 1 row (comb type microneedle) was used, and it was fixed on a micropositioner (manufactured by KEYENCE CORPORATION) while the needle tips were placed downward. The flat plate jig with a linear groove corresponding to the microneedle, which was obtained in Reference Example 2, was horizontally placed with a horizontal adjuster (manufactured by NISSIN MACHINE WORKS, LTD.). Ovalbumin (OVA) was used as an antigen, and 2 types of concentrations of aqueous OVA solutions (500 mg/mL, 500 mg/0.75 mL) were prepared. At this time, for clear view of the liquid surface, a fluorescent dye (carboxyfluorescein) was added thereto to color the aqueous solution to yellow. Each of the 2 types of aqueous OVA solutions with different concentrations was used separately for application of the small needles. The aqueous OVA solution was poured into the groove to allow the liquid surface of the aqueous solution to be raised higher than the jig surface in a convex manner. The small needles were placed such that the small needles were able to be immersed into the convex ridge of the raised liquid surface as shown in FIG. 10. The microneedle was lowered to immerse the small needles in the convex ridge of the aqueous solution as shown in FIG. 11. A setting was made such that only the small needles of the microneedle were immersed in the aqueous solution. Thereafter, the microneedle was pulled up and dried to obtain small needles to which OVA was applied.

The applied small needles were collected by means of breaking off or the like, and the applied part was re-dissolved into water. The concentration of the eluted protein was measured by a BCA protein assay reagent kit (manufactured by Thermo Fisher Scientific K.K.) to evaluate the amount of OVA carried in the small needles.

Thereby, the result shown in Table 1 described below is obtained.

TABLE 1

| Experiment No. | Concentration of Antigen (OVA) | carried Amount/ a Needle |
|---|---|---|
| 1 | 500 mg/mL | 0.27 µg |
| 2 | 667 mg/mL (500 mg/0.75 mL) | 0.32 µg |

As shown in Table 1, it is revealed that there is a substantial correlation between the carried amount of drug and the concentration of antigen in the aqueous solution. The result shows that the method of immersing small needles in the uniform surface of the aqueous solution (the ridge of the convex liquid surface) which is fixed due to surface tension in the narrow groove is a method of applying the drug liquid to the small needles precisely.

Moreover, since the aqueous solution is fixed due to surface tension in the linear groove, the ridge in the center part of the groove into which the small needles will be inserted is horizontal. Therefore, by lowering the microneedle horizontally, the adhesion of the aqueous solution to only the tips of the small needles is easily controlled visually. Consequently, it is easy to avoid that the aqueous solution adheres to extra parts (base of the small needles) other than the small needles.

Test Example 1

Administration Test for Mouse Using Drug-Applied Microneedle

Small needles to which a drug was applied were used for administration into the skin to confirm whether the medicinal effect was attained or not. As the drug, vaccines were supposed, and OVA was used as a model thereof. An in vivo test using mice was performed to confirm whether an antibody against OVA was produced in the mice or not.

Figure 12:
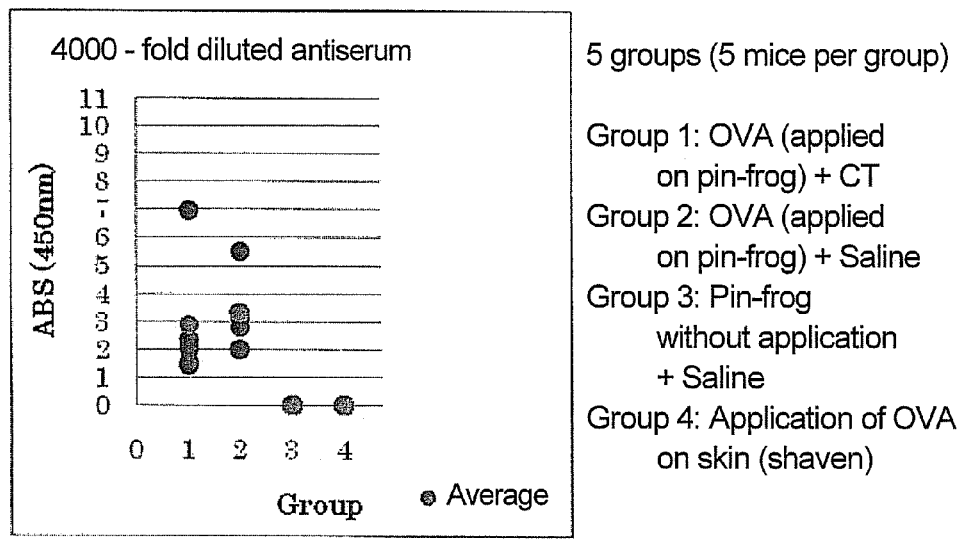
FIG. 12 is a graph showing a result of an administration test to mice by using a microneedle to which ovalbumin (OVA) is applied.

BALB/cAnN male mice (7 weeks of age), five mice in one group, were used. Under the existence of 1 µg non-toxic cholera toxin CT, an administration experiment was performed as follows. In accordance with Example 1, OVA-applied small needles were manufactured. The small needles were set in an administration device (JP patent application No. 2008-051335) and pressed on the abdomen of mice. Thereafter, the small needles were fixed with a tape (the needles were held on the skin for 2 days). Three weeks later, the second administration of OVA was performed similarly. One month later thereafter, the blood was collected, and the antibody titer in the blood was measured. As a result, antibody production was observed in the group of administration using the OVA-applied small needles, while it was not observed in the group of application of ovalbumin on the skin, as shown in FIG. 12.

As described above, it is clear that the administration using the OVA-applied small needles leads to antibody production, which shows that this small needle system is useful as a vaccine delivery system.

Example 2

Application of Drug Liquid to Small Needles of Microneedle (Array Type)

The microneedle obtained in Reference Example 1 was used. In accordance with Example 1, the microneedle was fixed on the micropositioner, and the flat plate jig obtained in Reference Example 2 was horizontally placed with the horizontal adjuster. In the same manner as in Example 1, as an antigen, the aqueous OVA solution (500 mg/mL) was poured into the grooves to allow the liquid surface of the aqueous solution to be raised higher than the jig surface in a convex manner due to surface tension of the aqueous solution. As shown in FIG. 10, the microneedle was lowered in the convex ridge of the raised liquid surface of the aqueous solution so that it was immersed into the convex ridge of the aqueous solution. Thereafter, the microneedle was pulled up and dried to obtain small needles to which OVA was applied, as shown in FIG. 14.

Reference Example 1

Manufacture of Microneedle (Array Type)

A microneedle made of silicon (a jig having a quadrangular prism shape, each 100 µm on a side, on which small needles having a length of 300 µm are vertically provided in an array of 10×10) was placed in a hot plate and heated at 80° C.

Figure 13:
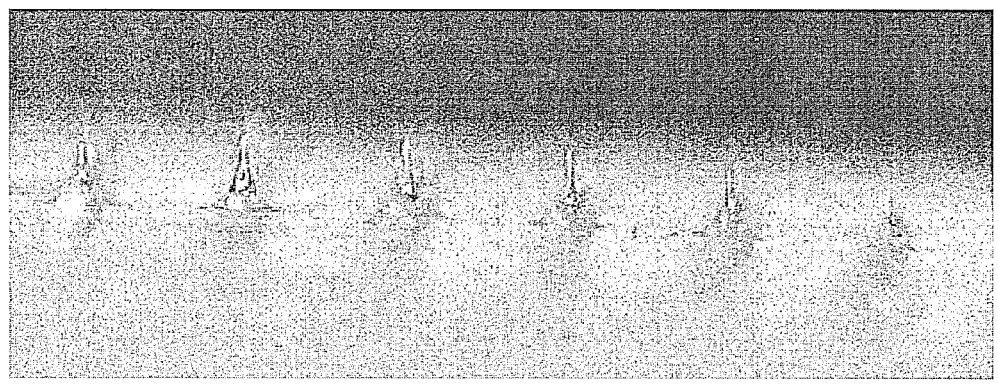
FIG. 13 is a perspective view (a magnified photograph) showing a microneedle made of polylactic acid.

A plate of polylactic acid (Mw: 10000) was placed on a flat plate (the surface to a downward direction) of a rheometer (EZ-TEST) manufactured by Shimadzu Corporation. Then, the flat plate was pulled down to bring the jig into contact with the sheet. After the flat plate was held at the position for about 7 seconds, the supporting-column was pulled upward at a rate of 10 mm/minute for about 2 mm and stopped. After 3 seconds of being stopped, the supporting-column was pulled upward at a rate of 500 mm/minute to obtain a micro array made of resin (microneedle) having acicular projections (small needles) of about 150 µm, as shown in FIG. 13.

Reference Example 2

Manufacture of Flat Plate Jig Made of Si with 10 Grooves

A photosensitive resist was coated onto a Si flat plate having a thickness of 500 µm by spin coating, and the following drawing pattern of grooves was drawn thereon by UV exposure:

(1) 10 linear grooves;
(2) the length of each groove is 2 cm;
(3) the pitch distance between the grooves is 800 μm;
(4) the width of each groove is 400 μm;
(5) the depth of each groove is 300 μm; and
(6) the grooves are connected to one another at both ends of each groove by the use of other grooves in order to level the ridge height of the convex liquid surface of each groove.

After the exposure, the photosensitive resist was developed by dipping to form openings corresponding to grooves. The drawing pattern was transferred onto the Si flat plate by inductively coupled plasma reactive ion etching (ICP-RIE) using $CF_4$ gas to cut the grooves. Here, the remaining photosensitive resist was removed by RIE using $O_2$ gas to obtain a flat plate jig made of Si with grooves.

Similarly, a flat plate jig made of Si having 11 grooves as shown in FIG. 8 can be manufactured.

Example 3

Application of Drug Liquid to Small Needles of Microneedle (Array Type) Using Jig for Application without Grooves The microneedle of 10×10 (array type) obtained in the same manner as in Reference Example 1 was used. In accordance with Example 1, the microneedle was fixed on the micropositioner, and the flat plate jig obtained in Reference Example 3 was horizontally placed with the horizontal adjuster. The aqueous OVA solution (500 mg/mL) was poured into the grooves. Thereby, it was possible to achieve the state as shown in FIG. 6, in which the drug liquid was filled between the hydrophobic films so that the liquid surface of the drug liquid was raised higher than the hydrophobic film surface in a convex manner.

Figure 7:
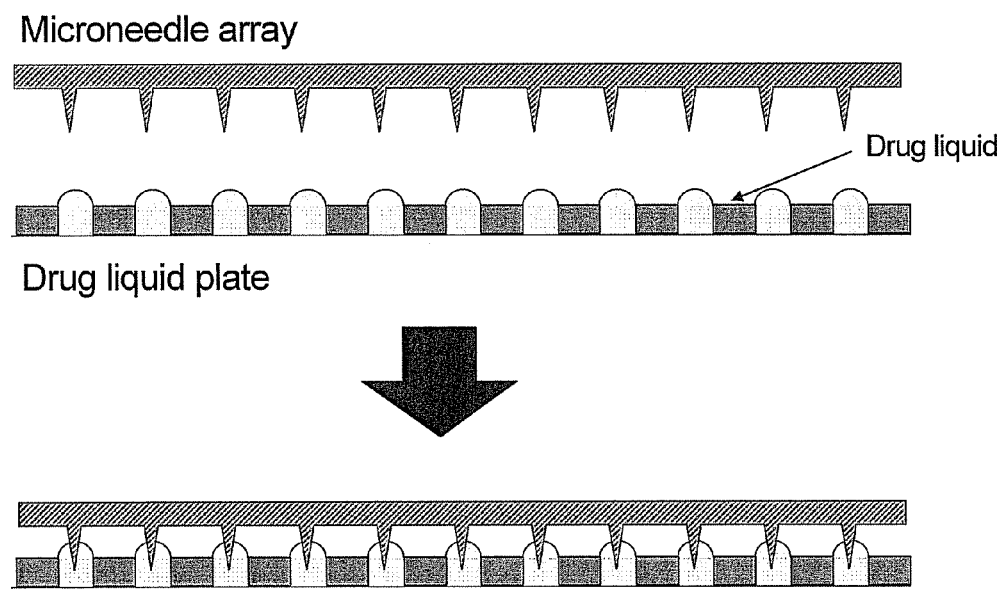
FIG. 7 is a schematic diagram showing the state when supplying a drug liquid to the grooves (white part) surrounded by the hydrophobic material (black part) illustrated in FIG. 6, allowing the liquid surface to be raised in a convex manner, and thereafter inserting and immersing a microneedle into the ridge of the convex liquid surface.

The microneedle was lowered in the convex ridge of the raised liquid surface of the drug liquid as shown in FIG. 7 so that it was immersed into the convex ridge of the aqueous solution. Thereafter, the microneedle was pulled up and dried to obtain small needles to which OVA was applied.

Reference Example 3

Manufacture of Jig without Grooves

A metal flat plate of stainless-steel was masked with the following drawing pattern, in which the black part was cut and the white part was left in FIG. 6:
(1) 11 linear grooves;
(2) the length of each groove is 1 cm;
(3) the pitch distance between the grooves is 0.8 mm; and
(4) the width of each groove is 300 μm.

A hydrophobic resin (Teflon (registered trademark)) was coated over the drawing pattern to form a film. The drawing pattern was removed, and the hydrophobic resin was dried. As a result, the jig shown in FIG. 6, in which the hydrophobic resin is applied and placed onto the black part, was manufactured.

INDUSTRIAL APPLICABILITY

According to the manufacturing method of the present invention, a microneedle to which a drug is uniformly applied can be obtained by immersing small needles of the microneedle into a drug liquid. Consequently, this makes it possible to achieve a method of manufacturing a microneedle with good quality, which is less likely to be affected by production environment (wind or vibration), in mass production with a simple device.

The invention claimed is:

1. A jig for allowing small needles of a microneedle to carry a liquid drug wherein
    (1) the jig has a roll-like shape with one or more liquid drug holding grooves, wherein
        (a) a pitch distance between the grooves is 300 to 1000 μm;
        (b) a width of each groove is 100 to 700 μm; and
        (c) a depth of each groove is 100 to 700 μm, and
    (2) the microneedle is a pin-frog-shaped plate having a size of 0.5 to 1.5 cm long and wide, on which 9 to 500 small needles are placed, wherein
        (a) the small needles of the microneedles are made of an aliphatic polyester selected from the group consisting of polylactic acid, polyglycolic acid, and a copolymer of lactic acid and glycolic acid,
        (b) the height of the small needles is 200 μm to 1 mm;
        (c) the maximum diameter of the base of the small needles is 50 μm to 500 μm;
        (d) the pitch distance between the small needles is 300 μm to 1 mm, and
        (e) the small needles are aligned in 3 to 30 horizontal rows and 3 to 30 vertical rows.

2. The roll-like jig according to claim 1, wherein the surface of the roll-like jig is coated with a hydrophobic material.

3. The roll-like jig according to claim 1, wherein the roll-like jig is made of silicon.

4. The roll-like jig according to claim 1, wherein the liquid drug holding groove has a cross sectional shape of an inverted triangle, a quadrangle, or a semicircle.

5. A method of carrying a liquid drug on small needles of a microneedle, comprising
    (i) providing a jig for allowing small needles of the microneedle to carry the liquid drug, wherein
        (1) the jig has a roll-like shape with one or more liquid drug holding grooves, wherein
            (a) a pitch distance between the grooves is 300 to 1000 μm,
            (b) a width of each groove is 100 to 700 μm, and
            (c) a depth of each groove is 100 to 700 μm, and
        (2) the microneedle is a pin-frog-shaped plate having a size of 0.5 to 1.5 cm long and wide, on which 9 to 500 small needles are placed, wherein
            (a) the small needles of the microneedle are made of an aliphatic polyester selected from the group consisting of polylactic acid, polyglycolic acid, and a copolymer of lactic acid and glycolic acid,
            (b) the height of the small needles is 200 μm to 1 mm;
            (c) the maximum diameter of the base of the small needles is 50 μm to 500 μm;
            (d) the pitch distance between the small needles is 300 μm to 1 mm, and
            (e) the small needles are aligned in 3 to 30 horizontal rows and 3 to 30 vertical rows,
    (ii) immersing the lower part of the roll of the jig in a liquid drug tank,
    (iii) rotating the roll of the jig,
    (iv) wiping off the liquid drug that has adhered to the roll surface of the jig with a plate-like tool so that the liquid drug is carried only in the liquid drug holding grooves,
    (v) setting the microneedle such that the small needles of the microneedle can be immersed in the liquid drug holding grooves in the upper part of the roll, whereby the small needles can pass through the liquid drug holding grooves in the upper part of the roll, and (vi) passing the small needles through the liquid drug holding grooves to allow adhesion of the liquid drug only to the surface of the small needles.

6. The method according to claim 5, wherein the surface of the roll-like jig is coated with a hydrophobic material.

7. The method according to claim 5, wherein the roll-like jig is made of silicon.

8. The method according to claim 5, wherein the liquid drug holding groove has a cross sectional shape of an inverted triangle, a quadrangle, or a semicircle.

9. The method according to claim 5, wherein the roll-like jig is made of metal.

10. The roll-like jig according to claim 1, wherein the roll-like jig is made of metal.

* * * * *